(12) United States Patent
Bertelsen

(10) Patent No.: US 9,351,903 B2
(45) Date of Patent: May 31, 2016

(54) EYE WASH DEVICE

(75) Inventor: Poul Bertelsen, Assens (DK)

(73) Assignee: Plum A/S, Assens (DK)

( * ) Notice: Subject to any disclaimer, the term of this patent is extended or adjusted under 35 U.S.C. 154(b) by 0 days.

(21) Appl. No.: 13/321,064

(22) PCT Filed: May 19, 2010

(86) PCT No.: PCT/EP2010/003054
§ 371 (c)(1),
(2), (4) Date: Nov. 17, 2011

(87) PCT Pub. No.: WO2010/133350
PCT Pub. Date: Nov. 25, 2010

(65) Prior Publication Data
US 2012/0071840 A1    Mar. 22, 2012

(30) Foreign Application Priority Data
May 19, 2009    (DE) ............... 20 2009 007 205 U

(51) Int. Cl.
*A61H 33/04*    (2006.01)
*A61H 35/02*    (2006.01)
*A61M 35/00*    (2006.01)
*B05B 15/04*    (2006.01)
*A61F 9/00*    (2006.01)

(52) U.S. Cl.
CPC .............. *A61H 35/02* (2013.01); *A61F 9/0008* (2013.01); *A61F 9/0026* (2013.01); *A61M 2210/0612* (2013.01); *B05B 15/0443* (2013.01)

(58) Field of Classification Search
CPC ..... A61F 9/0026; A61F 9/0008; A61H 35/02; A61M 2210/0612; B05B 15/0443
USPC ................... 604/295, 298, 300, 302
See application file for complete search history.

(56) References Cited

U.S. PATENT DOCUMENTS

| | | | |
|---|---|---|---|
| 4,012,798 A | | 3/1977 | Liautaud |
| 5,064,420 A | * | 11/1991 | Clarke et al. .................. 604/295 |
| 5,607,410 A | * | 3/1997 | Branch ......................... 604/302 |
| 5,762,606 A | * | 6/1998 | Minnich ....................... 600/205 |
| 5,795,342 A | | 8/1998 | Shapiro et al. |
| 5,921,444 A | * | 7/1999 | Fuchs ........................... 222/321.9 |
| 6,336,917 B1 | * | 1/2002 | Berke ........................... 604/295 |
| D672,870 S | | 12/2012 | Bertelsen |
| 2009/0288251 A1 | | 11/2009 | Strandberg et al. |
| 2010/0179580 A1 | * | 7/2010 | Oostman et al. ............. 606/187 |

FOREIGN PATENT DOCUMENTS

| | | |
|---|---|---|
| DE | 882 470 B | 7/1953 |
| DE | 911 654 B | 5/1954 |
| DE | 26 39 449 C3 | 4/1977 |

(Continued)

*Primary Examiner* — Tatyana Zalukaeva
*Assistant Examiner* — Andrew J Mensh
(74) *Attorney, Agent, or Firm* — Kelly & Kelley, LLP

(57) ABSTRACT

An eye rinsing device for rinsing at least one eye is embodied as an attachable attachment, which can be connected to a container, wherein the attachment can be placed onto the eye of a person. The eye rinsing device is provided with at least one rinsing opening, which is directed towards the eye by means of which the washing of an eye is carried out in an improved manner. The attachment encompasses a device having wing-like spreading elements which pull the upper eyelid and the lower eyelid apart so as to support the opening of the eye during the rinsing process.

9 Claims, 3 Drawing Sheets

(56) References Cited

FOREIGN PATENT DOCUMENTS

| | | |
|---|---|---|
| DE | 33 02 868 A1 | 8/1984 |
| DE | 83 02 343 U1 | 3/1985 |
| DE | 38 00 499 A1 | 7/1989 |
| DE | 694 13 673 T2 | 6/1999 |
| DE | 20 2006 008 877 U1 | 8/2006 |
| DE | 20 2007 002 927 U1 | 5/2007 |
| DE | 601 25 796 T2 | 10/2007 |
| WO | 87/02237 A1 | 4/1987 |
| WO | 2009/142912 A1 | 11/2009 |

* cited by examiner

EYE WASH DEVICE

TECHNICAL FIELD

The invention relates to an eye rinsing device according to the preamble of claim 1.

Eye rinsing devices serve to rinse one or both eyes, which have come into contact with chemicals or dust or dirt, respectively.

STATE OF THE ART

A portable eye washing apparatus for industrial use is known from patent specification DE 26 39 449 C3. It comprises a housing, which has a recess, which is dimensioned such that it can accommodate the head of a person, who uses the apparatus. The interior of the housing is embodied so as to be hollow and forms a container, in which a washing fluid is stored. Provision is made for a pair of nozzles in the housing on opposite sides. Each nozzle is turned slightly upwards, whereby the eyes can be sprayed and washed directly.

A further eye shower is known from DE 20 2006 008 877 U1. It comprises an injection device comprising an attachment element, which can be attached to commercial containers for non-alcoholic beverages. This eye shower consists of a one-piece molded part made of a plastic. This molded part encompasses an eye cup comprising an elliptical circumferential edge, by means of which the eye shower can be screwed to a bottle.

DE 20 2007 002 927 U1 shows and describes a different solution comprising a screw part or a bottle attachment, respectively, and an eye cup or an eye rinsing funnel, respectively. An unintentional discharge of the fluid is to be avoided hereby in the bottle area. A rinsing fluid can discharge from one or a plurality of discharge openings of the funnel. Provision is made between the bottle neck of the bottle and the bottle attachment of the eye shower for an additional sealing device.

A different eye rinsing bottle is presented in DE 33 02 868 A1. It has an eye cup, which is connected to a riser pipe. The riser pipe is embodied so as to be displaceable by means of a connecting nut and has a securing element at the end, which prevents a slipping of the riser pipe. DE 83 02 343 U1 describes a comparable construction comprising a riser pipe.

A different eye rinsing device is known from DE 100 39 446 A1, which can be combined with a container containing a rinsing fluid, to form an eye rinsing apparatus. This eye rinsing device has a small eye cup, which encompasses a ring, which is embodied for being placed onto the eye that is to be rinsed, and which is held by four arms. The device comprises a discharge opening for the fluid, which is located below the ring, and a pipe, which feeds the discharge opening.

The eye rinsing bottle, which is described in DE 38 00 499 A1, is also characterized by a funnel-shaped eye cup, which is arranged on a head piece. This rinsing device further comprises a feed pipe, which is connected to a head piece and which dips into a bottle, as well a shower-like discharge opening, through which the fluid of the feed pipe is guided, and a discharge hose, at which the fluid, which is sprayed out, can be drained.

An eye cup has the disadvantage that contaminations in the area of the eye cup can reach into the eye of the user. An eye rinsing device for avoiding this problem is known from DE 601 25 796 T2 or from DE 694 13 673 T2. The eye rinsing device has a bottle, which contains an eye fluid and which is sealed by means of a closing element. The device has a sleeve, which is surrounded by an eye cup and is thus protected against contamination by dust and dirt through this. An eye cup consisting of a bowl, in which at least one injection nozzle is integrated, is also used here. A container for a pressurized fluid comprising an outlet valve as well as a regulating element for regulating the fluid jet, which leaks at the valve, is used.

A different eye rinsing device is known from DE 882 470 B. One or two fluid jets, which stem from a pressurized fluid source and which are directed upwards at an acute angle to a person bending towards the fluid jets, is/are used, wherein the respective person spreads the eyes apart by hand. The device consists of a cup, above which an eye rinsing device is arranged.

The eye rinsing device described in DE 911 654 B has a storage container for a neutralizing fluid comprising a hose connector, which is connected to a shower, which can be rotated about an axis. An elevated shower position and an operating position are possible through this.

An eye funnel of a rinsing device, which can be screwed onto a bottle and which is to hold the eye open during the rinsing process, is described in WO 87/02237 A1.

ILLUSTRATION OF THE INVENTION: OBJECT, SOLUTION, ADVANTAGES

The invention is based on the object of creating an eye rinsing device, by means of which the rinsing of an eye is carried out in an improved manner.

This object is solved in that the attachment encompasses a device comprising wing-like spreading elements, which pull the upper eyelid and lower eyelid apart, so as to support the opening of the eye during the rinsing process.

The invention creates a first aid device for washing or rinsing, respectively, an eye, e.g. after the spraying of a chemical, such as acid, lye, solvents, toxins and the like.

The invention is based on the concept that, upon spraying a rinsing fluid into the eye, they eye is closed reflexively. In the case of known solutions, it is thus often necessary that the eyelids must be opened by hand. This has the disadvantage that one hand is used for spreading the eyelids and cannot be used for operating the eye rinsing device, e.g. for squeezing a bottle comprising a rinsing fluid. Other known solutions are not entirely suitable for spreading the eyelids.

The wings according to the invention act like two artificial auxiliary fingers, which keep both eyelids apart, so that the rinsing fluid can hit endangered eye areas unhindered.

An opening of the eyelids by hand is partially not possible in the case of eye funnels according to the state of the art, because the funnel forms a closed wall around the eye, so that a finger cannot touch the eyelids.

A further advantage of the invention is that an eye cup, which may not be sterile due to improper storage, is not present. Rinsing fluid cannot drain optimally in the case of eye cups, so that dirt that settled on the eye cup, can reach into the eye. In contrast, the fluid can drain optimally in the case of the solution according to the invention.

Further advantageous embodiments of the invention are characterized in the subclaims.

In an advantageous further development of the device according to the invention, provision is made for at least one rinsing opening to be directed such that it aims directly towards the tear duct and/or the surroundings thereof. Each device encompasses an attachment part, for example, comprising a small narrow opening, the arrangement and discharge or spray direction of which is embodied such that it aims directly towards the tear duct or the surroundings thereof, respectively.

In the case of a further advantageous embodiment of the invention, at least one rinsing opening is directed such that it aims directly towards the pupil and/or the surroundings thereof. Each attachment part encompasses one or a plurality of openings, for example, the design and the spray direction of which is/are arranged and embodied such that the rinsing fluid hits the pupil or the surroundings thereof, respectively.

A compact and handy embodiment of the eye rinsing device results from the attachment to be able to be attached directly onto a container, which is embodied as a bottle and which can be squeezed. By squeezing the bottle, the spray fluid can be sprayed from bottom to top or positionally independent and independent on the force of gravity, respectively.

A simple attachment to the bottle is possible in that the attachment is screwed to the bottle.

In the case of a further advantageous embodiment of the invention, the wing-like spreading elements can be deformed elastically or are made of a flexible material, respectively. When pressing the spreading elements onto the eye, these wings can open further, whereby an opening of the eye is supported. It is optimal for this when the wing-like spreading elements encompass a curved embodiment. The curve formed through this opens when being pressed onto the eye and relaxes when it is removed from the eye.

This opening movement becomes much softer when the wing-like spreading elements are provided with at least one crosswise groove for this purpose, so as to form a type of hinge joint, about which the open wing ends can be pivoted. The weak spot of the material, which is formed by the groove, provides for a bending of the wing with little force. The groove can be attached on one side or on two sides, so as to embody the hinge joint.

In an advantageous further development of the attachment according to the invention, provision is made for the wing-like spreading elements to be flattened or curved, respectively, at the open ends such that they are in an approximately parallel contact to the eyelid. The end sections of the wings in each case form a tongue, which rests flat against the eyelid, that is, on the upper or the lower lid.

So that the wings do not slip during the pressing, it is advantageous when a slip-resistant surface structure or profiling is arranged on the contact sides of the wing ends, which are directed towards the eyelids. A rubber-like surface, for example, can be integrally molded on the wing material as slip-resistant surface or small profiled bars, studs or the like, for example.

On principle, a single wing pair is sufficient to attain an opening movement of the eye. The wing pair consists of a first or upper wing, respectively, and a second or lower wing, respectively, so that each attachment is equipped with two wing pairs.

However, it is advantages for each attachment to be equipped with two wing pairs. This has the effect as if the eye were opened with four fingers or two hands, respectively, which is much safer.

BRIEF DESCRIPTION OF THE DRAWINGS

An exemplary embodiment will be defined in more detail by means of the drawings, wherein further advantageous developments of the invention and advantages thereof are described.

BEST MODE FOR CARRYING OUT THE INVENTION

Figure 1:
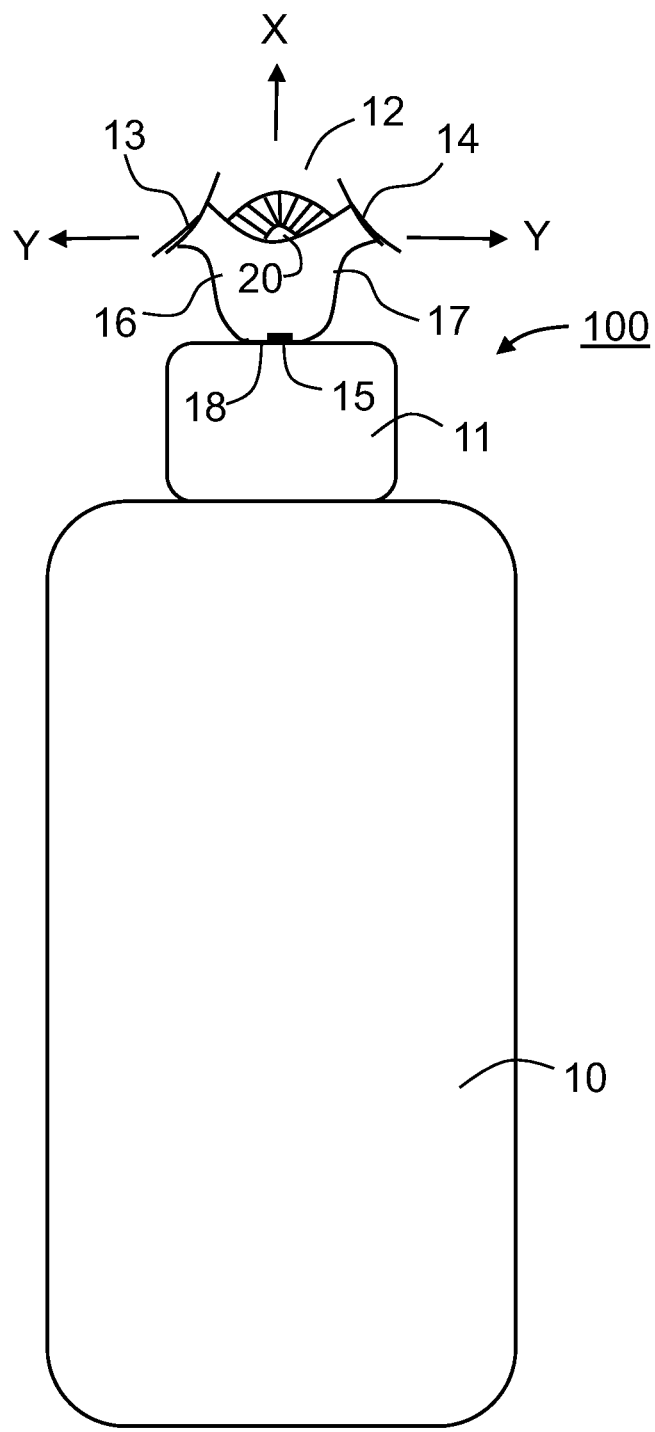
FIG. 1 shows an illustration of a device according to the invention, which is placed onto an eye.

The eye rinsing device 100 shown in FIG. 1 serves to rinse an eye, which has come into contact with a chemical, such as an acid, for example.

The device 100 is embodied with a container 10 as a connectable attachment 11. A suitable rinsing fluid, e.g. an aseptic solution, is contained in the container 10. As is illustrated in FIG. 1, the attachment 11 can be placed onto the eye 12, in particular onto the eyelids 13, 14 of a person.

For the discharge of the rinsing fluid, the attachment 11 is provided with at least one rinsing opening 15, which is directed towards the eye.

According to the invention, the attachment 11 encompasses a device comprising wing-like spreading elements 16, 17, which pull the upper eyelid 13 and the lower eyelid 14 apart, so as to support the opening of the eye during the rinsing process. Through this, it is not necessary to open the eyelids with two fingers.

One or a plurality of openings can be present in a discharge area 18. Preferably, at least one rinsing opening 15a (FIG. 3) is directed such that it aims directly towards the tear duct and/or the surroundings thereof. In the alternative or additionally, at least one other rinsing opening 15b (FIG. 3) is directed such that it aims directly towards the pupil 20 and/or the surroundings thereof.

As is shown in FIG. 1, the attachment can be placed directly onto a container 10, which is embodied as a bottle. The bottle can be made of a flexible plastic and can be squeezed, so that a sufficient rinsing pressure is created.

The attachment 11 has a thread, so that it can be screwed to the bottle.

The wing-like spreading elements 16, 17 can be deformed elastically. By pushing the bottle in the direction X of the eye, the wing ends 21, 22, which are illustrated in more detail in FIG. 2, thus automatically move in the direction of the arrow Y or in opposite direction, respectively, as is shown by means of the arrows Y.

The wing-like spreading elements 16, 17 encompass a curved embodiment. The curve base 23 is connected in one piece to a cap-shaped part 24 of the attachment 11, namely such that it projects laterally. A reinforcement bar 25 additionally connects the spreading element 16 to the cap-shaped part 24.

Each of the wing-like spreading elements 16, 17 is provided with at least one groove 26, which is directed at right angles, so as to form a type of hinge joint, about which the open wing end 21, 22 can be pivoted. The groove is located between the curve base 23 and the wing end, namely approximately still in the lower area of the wing or on approximately ⅓ of the distance to the wing end 21.

On the edges, the wing ends are provided with a bulge 27, which forms a soft flange, so that the eye cannot be damaged.

Figure 2:
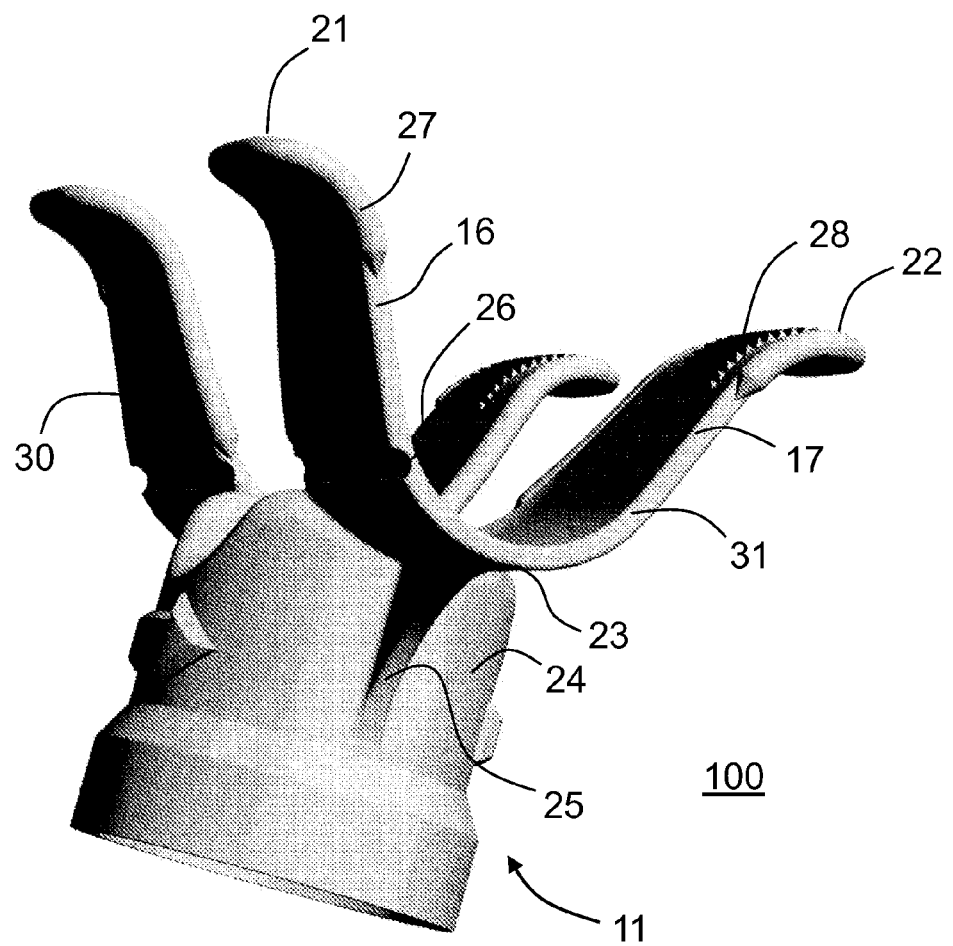
FIG. 2 shows a perspective illustration of an attachment of the device and FIG. 3 shows a further illustration of the attachment.

As is shown in FIGS. 1 and 2, the wing-like spreading elements 16, 17 are flattened or curved, respectively, at the open ends 21, 22 such that they are in an approximately parallel contact to the eyelids 13, 14. The pressure in direction X is thus distributed across a larger surface, which is more comfortable for the user.

FIG. 2 shows that a slip-resistant surface structure or profiling 28 is arranged on the contact sides of the wing ends 21, 22, which are directed towards the eyelids 13, 14. It is formed by small bars, which have a triangular profile.

Overall, the attachment 11 has two wing pairs 30, 31, so that four wings are available. The wing pairs 30, 31 are arranged spaced apart from one another, so that a gap of the width of one wing, for example, is created. The rinsing fluid can drain optimally through this gap, without having to touch one of the wings, which is advantageous when the wings are contaminated.

Figure 3:
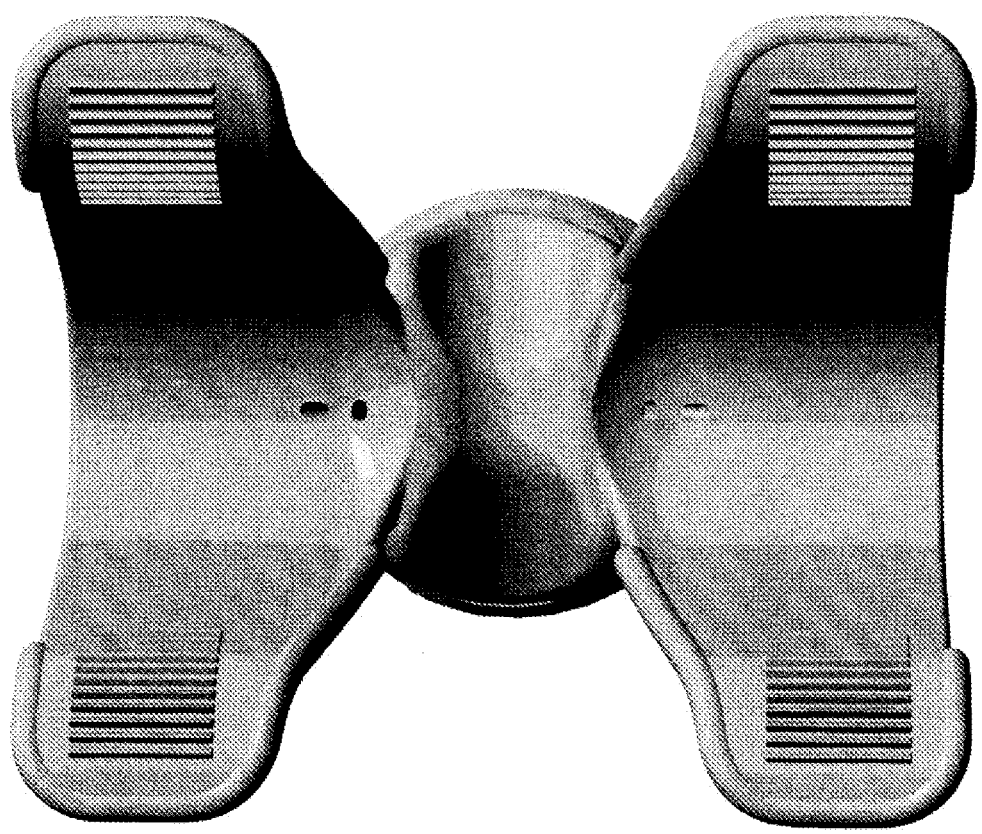

As is shown in FIG. 3, the spreading elements 16, 17 narrow towards their ends 21, 22.

The invention is not limited to this example. For instance, the rinsing pressure can also be created by means of the force of gravity or by means of a motor. The eye rinsing device can also be provided for rinsing the eye with a medical solution or a different fluid, for example in the case of conjunctivitis. Instead of a spray jet, drops can also fall onto the eye, for example medical eye drops. The terms rinsing, rinsing opening and rinsing process can also be used for dripping processes, so that the device according to the invention can equivalently also be used for an eye dripping device. The device can also be embodied for one eye or for both eyes.

LIST OF REFERENCE NUMERALS

10 container
11 attachment
12 eye
13, 14 eyelids
15 rinsing openings
16, 17 spreading elements
18 discharge area
19 - - -
20 pupil
21, 22 wing ends
23 curve base
24 cap-shaped part
25 reinforcement bar
26 groove
27 bulge
28 profiling
29 - - -
30, 31 wing pairs
100 eye rinsing device

The invention claimed is:

1. An eye rinsing device for rinsing at least one eye, comprising:
an attachment which can be directly mounted on a bottle which can be squeezed, wherein the attachment can be placed onto the eye of a person;
wherein the attachment includes a member comprising wing-like spreading elements which pull an upper eyelid and a lower eyelid apart so as to support the opening of the eye during a rinsing process;
characterized in that the attachment is provided with at least one rinsing opening which is directed towards the eye, whereas the at least one rinsing opening is directed such that it aims towards a tear duct and/or a pupil of the eye, wherein the member is provided with one wing pair, whereby the wing pair consists of a first upper wing and a second lower wing, wherein the wing-like spreading elements are provided with at least one crosswise groove so as to form a type of hinge joint about which the open wing ends can be pivoted, wherein the groove is located between a curve base of the wing-like spreading elements and the wing end ⅓ of the distance to the wing end, wherein no eye cup is present so that an optimal draining of rinsing fluid is achieved by means of the wing pair allowing rinsing fluid to drain to at least two opposing sides of the member pulling the upper eyelid and the lower eyelid apart, wherein the wing-like spreading elements comprise a plurality of arms connected to each other at the curve base, each arm having a free end for pulling the eye lids apart, and wherein the at least one rinsing opening arranged at a central portion of the curve base.

2. An eye rinsing device for rinsing at least one eye, comprising:
an attachment which can be directly mounted on a bottle which can be squeezed, wherein the attachment can be placed onto the eye of a person;
wherein the attachment comprises wing-like spreading elements which pull an upper eyelid and a lower eyelid apart so as to support the opening of the eye during a rinsing process;
characterized in that the attachment is provided with at least one rinsing opening which is directed towards the eye, whereas the at least one rinsing opening is directed such that it aims towards a tear duct and/or a pupil of the eye, wherein no eye cup is present and the attachment is provided with two wing pairs being spaced apart from one another for forming a gap so that rinsing fluid can drain optimally through this gap without having to touch one of the wings, wherein the wing-like spreading elements comprise a plurality of arms each having a free end for pulling the eye lids apart, and wherein the at least one rinsing opening is arranged at a central portion of a curve base of the wing-like spreading elements.

3. The eye rinsing device according to either of claim 1 or 2, characterized in that the wing-like spreading elements can be deformed elastically.

4. The eye rinsing device according to either of claim 1 or 2, characterized in that the wing-like spreading elements encompass a curved embodiment.

5. The eye rinsing device according to either of claims 1 or 2, characterized in that the wing-like spreading elements are flattened or curved, respectively, at the open wing ends such that they are in an approximately parallel contact to the upper eyelid and/or the lower eyelid.

6. The eye rinsing device according to claim 5, characterized in that a slip-resistant surface structure or profiling is arranged on contact sides of the open wing ends which are directed towards the upper eyelid and/or the lower eyelid.

7. The eye rinsing device according to claim 1, characterized in that each attachment is equipped with two wing pairs.

8. The eye rinsing device according to either of claims 1 or 2, characterized in that the attachment can be screwed to the bottle.

9. The eye rinsing device according to claim 2, wherein the wing-like spreading elements are provided with at least one crosswise groove so as to form a type of hinge joint about which the open wing ends can be pivoted, wherein the groove is located between the curve base of the wing-like spreading elements and the wing end ⅓ of the distance to the wing end.

* * * * *